(12) United States Patent
Yamada et al.

(10) Patent No.: US 9,393,445 B2
(45) Date of Patent: Jul. 19, 2016

(54) RADIATION THERAPY DEVICE CONTROLLER, PROCESSING METHOD AND PROGRAM FOR SAME

(75) Inventors: Masahiro Yamada, Tokyo (JP); Yasunobu Suzuki, Tokyo (JP); Kunio Takahashi, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 304 days.

(21) Appl. No.: 13/994,986

(22) PCT Filed: Oct. 24, 2011

(86) PCT No.: PCT/JP2011/074395
§ 371 (c)(1),
(2), (4) Date: Jun. 17, 2013

(87) PCT Pub. No.: WO2012/127724
PCT Pub. Date: Sep. 27, 2012

(65) Prior Publication Data
US 2013/0274539 A1    Oct. 17, 2013

(30) Foreign Application Priority Data

Mar. 18, 2011   (JP) ................................. 2011-061024

(51) Int. Cl.
*A61N 5/10*   (2006.01)

(52) U.S. Cl.
CPC ............ *A61N 5/1039* (2013.01); *A61N 5/1049* (2013.01); *A61N 5/1067* (2013.01); *A61N 2005/1054* (2013.01); *A61N 2005/1059* (2013.01); *A61N 2005/1062* (2013.01)

(58) Field of Classification Search
CPC .................... G06T 11/003; A61N 2005/1061; A61N 5/1049; A61N 2005/1052; A61B 6/5288; A61B 6/541; A61B 6/032

USPC ................................................... 600/300, 1–2
See application file for complete search history.

(56) References Cited

U.S. PATENT DOCUMENTS 5,901,199 A    5/1999  Murphy et al.
2003/0128801 A1*  7/2003  Eisenberg et al. .............. 378/19

(Continued)

FOREIGN PATENT DOCUMENTS

CN          101076282 A    11/2007
JP          2003-117010 A    4/2003

(Continued)

OTHER PUBLICATIONS

European Search Report mailed Jun. 16, 2014 for related Application No. 11861482.5.

(Continued)

*Primary Examiner* — Samuel Gilbert
(74) *Attorney, Agent, or Firm* — Birch, Stewart, Kolasch & Birch, LLP

(57) ABSTRACT

This radiation therapy device controller selects, for a plurality of body motion phases, computed tomography image data obtained which shows a diseased portion, and generates, for each rotation angles of a ray source and a sensor array, a reconstructed image. The control device generates a radiation projection image which shows the diseased portion when the radiation is radiated if the rotation angle is a predetermined rotation angle, compares the reconstructed image of each of the plurality of body motion phases with the radiation projection image, and determines a body motion phase indicated by a reconstructed image in which a difference is small, to be a current respiratory phase. As a result, a position of the diseased portion calculated for the computed tomography image data in the computed tomography image data group of the respiratory phase in advance is identified to be a current position of the diseased portion.

2 Claims, 8 Drawing Sheets

(56) References Cited

U.S. PATENT DOCUMENTS

| | | |
|---|---|---|
| 2006/0074292 A1 | 4/2006 | Thomson et al. |
| 2006/0079754 A1* | 4/2006 | Welch et al. .................. 600/410 |
| 2010/0119032 A1 | 5/2010 | Yan et al. |

FOREIGN PATENT DOCUMENTS

| | | |
|---|---|---|
| JP | 3708434 B2 | 10/2005 |
| JP | 2008-514352 A | 5/2008 |
| JP | 2008-154861 A | 7/2008 |
| JP | 4126318 B2 | 7/2008 |
| JP | 4444338 B2 | 3/2010 |
| JP | 2010-246883 A | 11/2010 |
| JP | 2012-196259 A | 10/2012 |

OTHER PUBLICATIONS

Chinese Office Action mailed Feb. 17, 2015 for Chinese Application No. 201180060994.0 with an English Translation.

International Search Report issued in PCT/JP2011/074395, dated Jan. 17, 2012.

Written Opinion of the International Searching Authority issued in PCT/JP2011/074395, dated Jan. 17, 2012.

Decision to Grant for corresponding EP Application No. 11861482.5 dated Jul. 30, 2015.

* cited by examiner

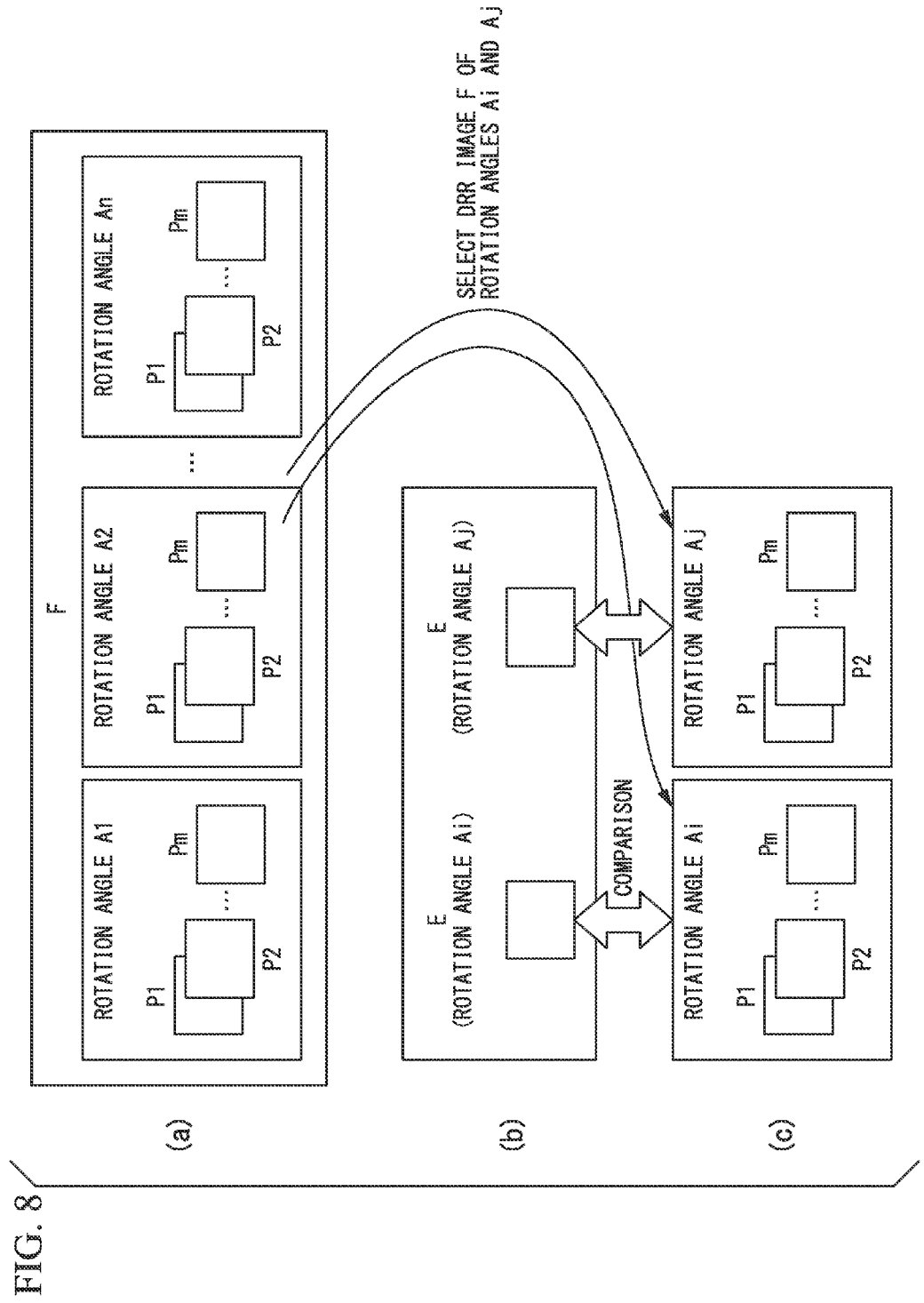

RADIATION THERAPY DEVICE CONTROLLER, PROCESSING METHOD AND PROGRAM FOR SAME

TECHNICAL FIELD

The present invention relates to a radiation therapy device controller that tracks a position of a diseased portion in a living body, and a processing method and program for the same. Priority is claimed on Japanese Patent Application No. 2011-061024, filed Mar. 18, 2011, the content of which is incorporated herein by reference.

BACKGROUND ART

A radiation therapy device controller identifies a radiation irradiation position in a living body based on a position of a diseased portion (tumor) displayed on a CT image (a computed tomography image) and transmits the position to the radiation therapy device. Accordingly, the radiation therapy device irradiates a diseased portion in the living body with radiation based on a radiation irradiation position received from a radiation therapy device controller to perform treatment. Here, a position of the diseased portion such as a tumor in the living body varies due to influence of respiration or the like. Accordingly, it is necessary to accurately track the position of the diseased portion varying in the living body in order to improve the accuracy of irradiation of radiation to an irradiation position of the diseased portion. In Patent Document 1, technology for designating a diseased portion area in a radiation projection image (transmission image) and irradiating the diseased portion with radiation based on the diseased portion area is described (See Patent Document 1).

PRIOR ART DOCUMENT

Patent Document

Patent Document 1: Japanese Patent No. 4126318

SUMMARY OF INVENTION

Problem to be Solved by the Invention

However, in a radiation projection image (transmission image), a resolution of a diseased portion is likely to be low and identifying a position of the diseased portion is likely to be difficult. High accuracy of tracking a diseased portion varying within the living body has been desired.

An object of the present invention is to provide a radiation therapy device controller, and a processing method and program for the same that are capable of solving the problems described above.

Means for Solving the Problem

A first aspect of the present invention is a radiation therapy device controller for controlling a radiation therapy device that irradiates a living body arranged between a ray source and a sensor array with radiation from the ray source to treat a diseased portion of the living body, the control device including: a CT image selection unit that selects, for each of a plurality of body motion phases of the living body, CT image data from a CT image data group generated for each of the plurality of body motion phases of the living body; a reconstructed image generation unit that generates, for each rotation angles of the ray source and the sensor array, a reconstructed image corresponding to the body motion phase using the selected CT image data; a radiation projection image generation unit that generates a radiation projection image which shows the diseased portion when the radiation is radiated from the ray source to the sensor array if the rotation angle is a predetermined rotation angle; a body motion phase determination unit that compares the reconstructed image of each of the plurality of body motion phases with the generated radiation projection image, and determines a body motion phase indicated by a reconstructed image in which a difference between luminances of pixels constituting the images is small, to be a current body motion phase of the living body; and a diseased portion tracking processing unit that identifies a position of the diseased portion calculated for the CT image data in the CT image data group of the current body motion phase of the living body in advance, and determines the identified position to be a current position of the diseased portion.

The radiation projection image generation unit may generate radiation projection images for a plurality of predetermined rotation angles. As a result, the body motion phase determination unit may determine, in comparison of the reconstructed image and the radiation projection image, a body motion phase indicated by a reconstructed image used for the comparison when a value of a sum of differences of the reconstructed image and the radiation projection image of the same body motion phase for the plurality of predetermined rotation angles is smallest, to be the current body motion phase of the living body.

The body motion phase determination unit may determine, in comparison of the reconstructed image and the radiation projection image, a body motion phase indicated by a reconstructed image used for the comparison when a value of a sum of luminance differences of all pixels of the reconstructed image and the radiation projection image of the same body motion phase for the plurality of predetermined rotation angles is smallest, to be the current body motion phase of the living body.

The body motion phase determination unit may perform comparison of the reconstructed image and the radiation projection image. As a result, the body motion phase determination unit may determine a body motion phase indicated by a reconstructed image used for the comparison when a value of a sum of luminance differences in a pixel range in which a luminance change is great when a body motion phase is changed among pixels of the reconstructed image and the radiation projection image of the same body motion phase for the plurality of predetermined rotation angles is smallest, to be the current body motion phase of the living body.

Further, according to a second aspect of the present invention, the radiation therapy device controller selects, as CT image data of an update target, CT image data of a set body motion phase from a CT image data group generated for each body motion phase in advance, and generates a radiation projection image corresponding to each rotation angle. The control device records the radiation projection image, the rotation angle when rotating the ray source and the sensor array at the time of generating the radiation projection image, and a body motion phase at the time of generating the radiation projection image to be correlated with each other, and detects the rotation angle at the time of generating the radiation projection image. The control device generates a reconstructed image when the CT image data of the update target is projected from the ray source to the sensor array at the detected rotation angle, and compares each pixel of the radiation projection image with each pixel of the generated reconstructed image to generate difference information indicating a luminance difference for the respective pixels. The control device identifies, in the CT image data of the update target, a pixel on a straight line connecting the ray source and a detection element of the sensor array, and calculates a luminance update amount candidate value for each identified pixel based on a degree of easiness of change in the luminance value of the identified pixel and the difference information. As a result, the control device calculates a luminance update amount of each identified pixel using the luminance update amount candidate value of each identified pixel calculated for a plurality of rotation angles corresponding to the body motion phase that is a target, and updates a luminance value of each corresponding pixel of the CT image data of the update target, using the luminance update amount of each identified pixel.

Further, a third aspect of the present invention is a processing method for a radiation therapy device controller for controlling a radiation therapy device that irradiates a living body arranged between a ray source and a sensor array with radiation from the ray source to treat a diseased portion of the living body. CT image data is selected, for each of a plurality of body motion phases of the living body, from a CT image data group generated for each of the plurality of body motion phases of the living body, and a reconstructed image corresponding to the body motion phase is generated, for each rotation angles of the ray source and the sensor array, using the selected CT image data. If the rotation angle is a predetermined rotation angle, a radiation projection image is generated which shows the diseased portion when the radiation is radiated from the ray source to the sensor array, the reconstructed image of each of the plurality of body motion phases is compared with the generated radiation projection image, and a body motion phase indicated by a reconstructed image in which a difference between luminances of pixels constituting the images is small is determined to be a current body motion phase of the living body. A position of the diseased portion calculated for the CT image data in the CT image data group of the current body motion phase of the living body in advance is identified and determined to be a current position of the diseased portion.

Further, a fourth aspect of the present invention is a program for controlling a radiation therapy device that irradiates a living body arranged between a ray source and a sensor array with radiation from the ray source to treat a diseased portion of the living body. The program causes a computer of a radiation therapy device controller to function as: a CT image selection device that selects, for each of a plurality of body motion phases of the living body, CT image data from a CT image data group generated for each of the plurality of body motion phases of the living body; a reconstructed image generation device that generates, for each rotation angles of the ray source and the sensor array, a reconstructed image corresponding to the body motion phase using the selected CT image data; a radiation projection image generation device that generates a radiation projection image which shows the diseased portion when the radiation is radiated from the ray source to the sensor array if the rotation angle is a predetermined rotation angle; a body motion phase determination device that compares the reconstructed image of each of the plurality of body motion phases with the generated radiation projection image, and determines a body motion phase indicated by a reconstructed image in which a difference between luminances of pixels constituting the images is small, to be a current body motion phase of the living body; and a diseased portion tracking processing device that identifies a position of the diseased portion calculated for the CT image data in the CT image data group of the current body motion phase of the living body in advance, and determines the identified position to be the current position of the diseased portion.

Effect of the Invention

According to the present invention, it is possible to improve the accuracy of tracking a diseased portion moving in the living body since a current respiratory phase is sequentially identified using the sequentially generated radiation projection image and the DRR image generated from CT image data, and the diseased portion position identified in advance for the CT image corresponding to the identified respiratory phase is identified as a current diseased portion position.

BRIEF DESCRIPTION OF DRAWINGS

FIG. 8 is a diagram illustrating an overview of the diseased portion tracking process.

DESCRIPTION OF EMBODIMENTS

Hereinafter, a radiation therapy device controller, and a radiation therapy device controlled by the radiation therapy device controller according to an embodiment of the present invention will be described.

An embodiment of the present invention is assumed to create CT image data for each body motion phase of a periodic body motion such as respiration or heartbeat. However, a description in which only a respiratory phase is a target of the body motion will be given hereinafter for simplification.

Figure 1:
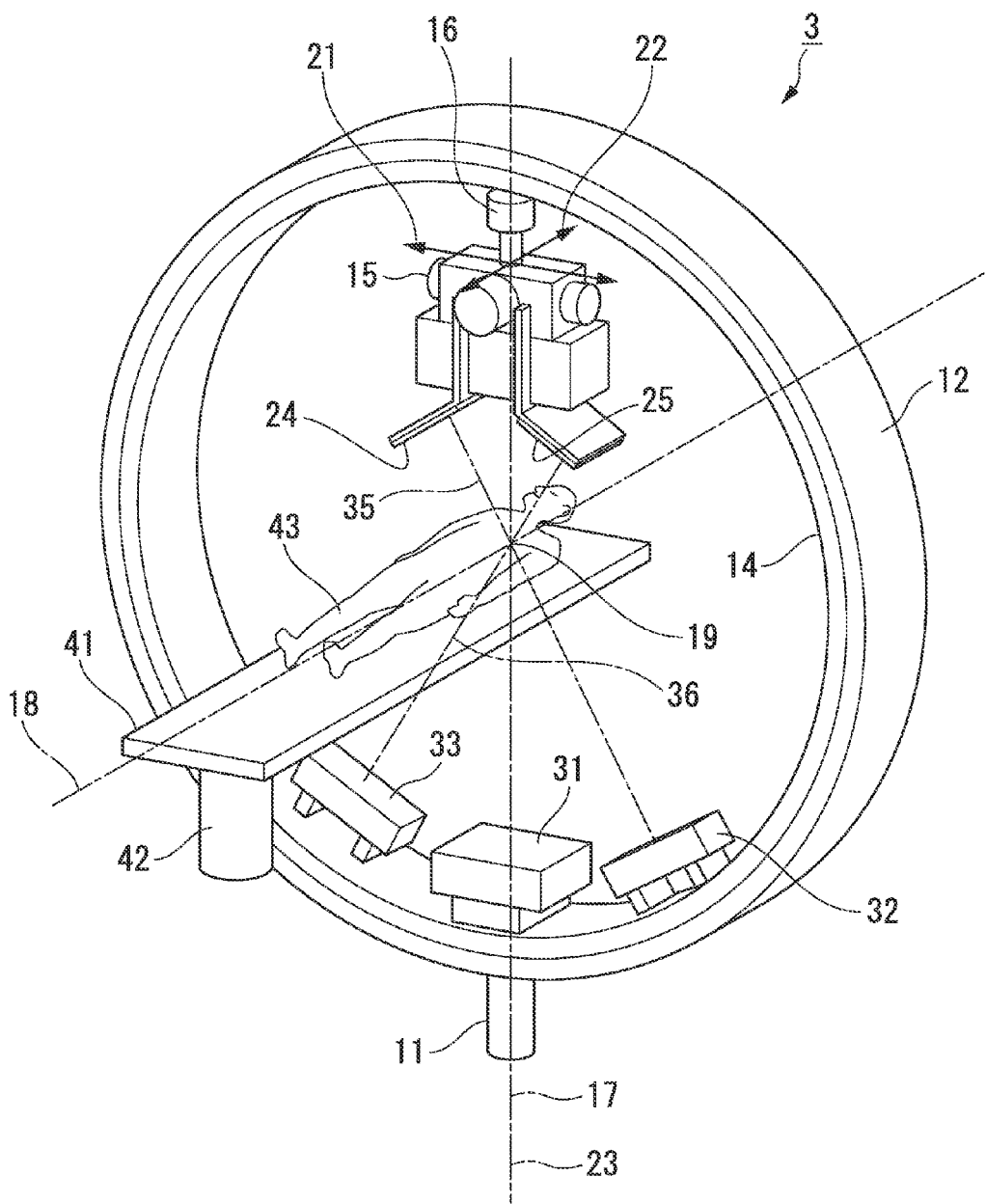
FIG. 1 is a diagram illustrating a configuration of a radiation therapy device.

First, an overview of the radiation therapy device that is a control target will be described. FIG. 1 shows a radiation therapy device.

As shown in FIG. 1, a radiation therapy device 3 includes a swivel driving device 11, an O ring 12, a traveling gantry 14, a head swing mechanism 15, and a therapeutic radiation irradiation device 16. The swivel driving device 11 supports the O ring 12 against a base to be rotatable around a rotation axis 17, and rotates the O ring 12 around the rotation axis 17 under control of the radiation therapy device controller 1. The rotation axis 17 is parallel to a vertical direction. The O ring 12 is formed in a ring shape around a rotation axis 18 and supports the traveling gantry 14 to be rotatable around the rotation axis 18. The rotation axis 18 is perpendicular to the vertical direction and passes through an isocenter 19 included in the rotation axis 17. Further, the rotation axis 18 is fixed with respect to the O ring 12. That is, the rotation axis 18 is rotated around the rotation axis 17 together with the O ring 12. The traveling gantry 14 is formed in a ring shape around the rotation axis 18, and arranged to be concentric with the ring of the O ring 12. Further, the radiation therapy device 3 includes a traveling driving device, which is not shown. The traveling driving device rotates the traveling gantry 14 around the rotation axis 18 under control of the radiation therapy device controller 1.

The therapeutic radiation irradiation device 16 is arranged at an inward side of the traveling gantry 14. The therapeutic radiation irradiation device 16 radiates therapeutic radiation 23 under control of the radiation therapy device controller 1.

The head swing mechanism 15 is fixed to an inward side of the ring of the traveling gantry 14 and supports therapeutic radiation irradiation device 16 against the traveling gantry 14. The head swing mechanism 15 has a pan axis 21 and a tilt axis 22. The pan axis 21 is fixed to the traveling gantry 14, and is parallel to the rotation axis 18 without intersecting the rotation axis 18. The tilt axis 22 is fixed to the traveling gantry 14 and orthogonal to the pan axis 21. The head swing mechanism 15 rotates the therapeutic radiation irradiation device 16 around the pan axis 21 and rotates the therapeutic radiation irradiation device 16 around the tilt axis 22 under control of the radiation therapy device controller 1.

As the therapeutic radiation irradiation device 16 is supported by the traveling gantry 14 as described above, the therapeutic radiation 23 always substantially passes through the isocenter 19 even when the O ring 12 is rotated by the swivel driving device 11 or the traveling gantry 14 is rotated by the traveling driving device if the therapeutic radiation irradiation device 16 is first adjusted to be directed to the isocenter 19 by the head swing mechanism 15. That is, the therapeutic radiation 23 can be radiated from an arbitrary direction to the isocenter 19 by performing the traveling and the swivel. Further, since the therapeutic radiation irradiation device 16 or the like is a heavy object, there are cases in which the O ring itself is mechanically deformed according to the traveling and the swivel. Also, there are cases in which the diseased portion does not necessarily match the isocenter. In such cases, the therapeutic radiation irradiation device 16 may be adjusted to be directed to the isocenter 19 or the diseased portion by the head swing mechanism 15 again, subsequent to setting of the traveling and the swivel.

Further, the radiation therapy device 3 includes a plurality of imager systems. That is, the radiation therapy device 3 includes diagnostic X-ray sources 24 and 25 and sensor arrays 32 and 33.

The diagnostic X-ray source 24 is supported by the traveling gantry 14. The diagnostic X-ray source 24 is arranged at the inward side of the ring of the traveling gantry 14 and arranged in such a position that an angle formed by a line segment connecting the isocenter 19 and the diagnostic X-ray source 24 and a line segment connecting the isocenter 19 and the therapeutic radiation irradiation device 16 is an acute angle. The diagnostic X-ray source 24 radiates a diagnostic X-ray 35 toward the isocenter 19 under control of the radiation therapy device controller 1. The diagnostic X-ray 35 is a cone-beam in a cone shape radiated from one point of the diagnostic X-ray source 24 and having the point as a vertex. The diagnostic X-ray source 25 is supported by the traveling gantry 14. The diagnostic X-ray source 25 is arranged at the inward side of the ring of the traveling gantry 14 and arranged in such a position that an angle formed by a line segment connecting the isocenter 19 and the diagnostic X-ray source 25 and a line segment connecting the isocenter 19 and the therapeutic radiation irradiation device 16 is an acute angle. The diagnostic X-ray source 25 radiates a diagnostic X-ray 36 toward the isocenter 19 under control of the radiation therapy device controller 1. The diagnostic X-ray 36 is a cone-beam in a cone shape radiated from one point of the diagnostic X-ray source 25 and having the point as a vertex.

The sensor array 32 is supported by the traveling gantry 14. The sensor array 32 receives the diagnostic X-ray 35 that is radiated by the diagnostic X-ray source 24 and then transmitted through a subject around the isocenter 19, and generates a radiation projection image of the subject. The sensor array 33 is supported against the traveling gantry 14. The sensor array 33 receives the diagnostic X-ray 36 that is radiated by the diagnostic X-ray source 25 and then transmitted through the subject around the isocenter 19, and generates a radiation projection image of the subject. A FPD (Flat Panel Detector) and an X ray II (Image Intensifier) are exemplified as the sensor arrays 32 and 33.

According to such imager systems, it is possible to generate the radiation projection image centered on the isocenter 19 based on image signals obtained by the sensor arrays 32 and 33.

The radiation therapy device 3 further includes a sensor array 31. The sensor array 31 is arranged in such a manner that a line segment connecting the sensor array 31 and the therapeutic radiation irradiation device 16 passes through the isocenter 19 and is fixed to the inward side of the ring of the traveling gantry 14. The sensor array 31 receives the therapeutic radiation 23 that is radiated by the therapeutic radiation irradiation device 16 and transmitted through the subject around the isocenter 19, and generates a radiation projection image of the subject. An FPD (Flat Panel Detector) or an X ray II (Image Intensifier) is exemplified as the sensor array 31.

When the traveling gantry 14 is caused to travel along the O ring 12, the diagnostic X-ray source 24 and the sensor array 32, the diagnostic X-ray source 25 and the sensor array 33, and the therapeutic radiation irradiation device 16 and the sensor array 31 can be rotated around the rotation axis 18 passing through the isocenter 19 while maintaining a positional relationship. A rotation angle around the rotation axis 18 of the traveling gantry 14, the diagnostic X-ray sources 24 and 25, the therapeutic radiation irradiation device 16 and the sensor arrays 31 to 33 relative to a predetermined position is hereinafter referred to simply as a rotation angle.

Further, the radiation therapy device 3 includes a treatment table 41 and a treatment table driving device 42. The treatment table 41 is used for a patient 43 being treated to lie on. The treatment table 41 includes a fastener, which is not shown. This fastener secures the patient to the treatment table 41 so that the patient does not move. The treatment table driving device 42 supports the treatment table 41 against a base and moves the treatment table 41 under control of the radiation therapy device controller 1.

Further, the radiation therapy device 3 includes an infrared camera, which is not shown, and detects a motion of an infrared marker attached to the living body using the infrared camera. The infrared marker performs a periodic motion in a period and a phase corresponding to a respiratory period and phase in the living body. When the radiation therapy device 3 irradiates the living body with radiation under the control of the radiation therapy device controller 1, the radiation therapy device 3 extracts the phase in the periodic motion of the infrared marker from the detected motion of the infrared marker, and notifies the radiation therapy device controller 1 of data of the extracted phase as information relating to the respiratory phase. Also, the radiation therapy device controller 1 generates CT image data based on the radiation projection image according to the initially set CT image data group, the different respiratory phases, and the plurality of rotation angles.

Figure 2:
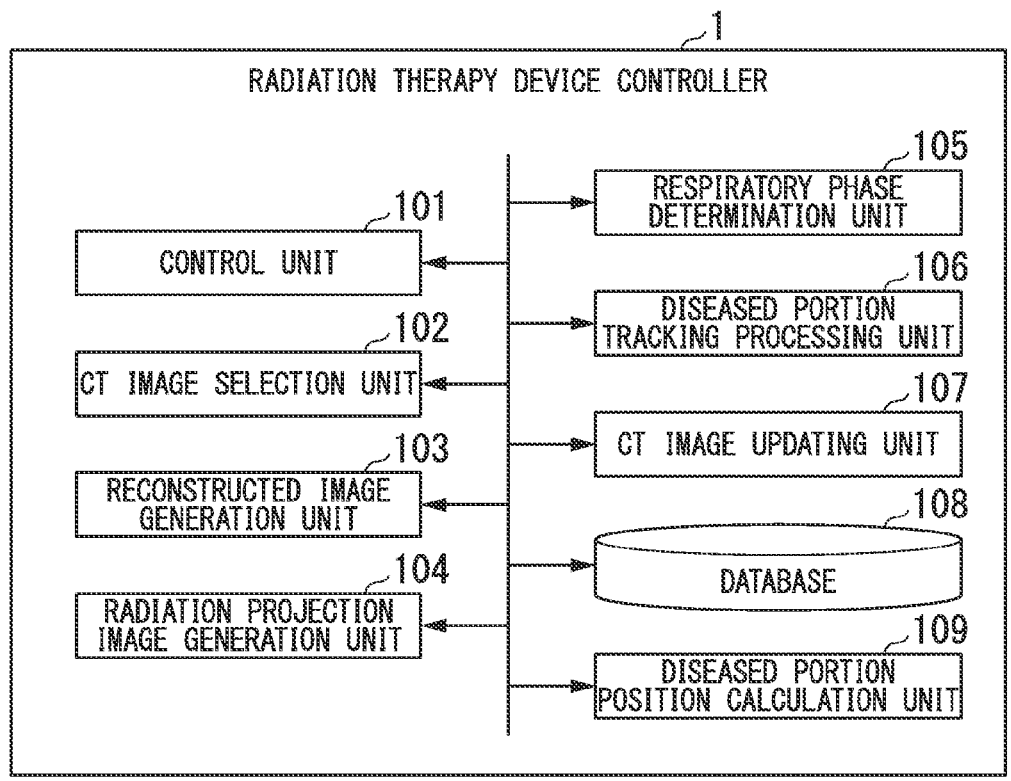
FIG. 2 is a block diagram illustrating a configuration of a radiation therapy device controller.

FIG. 2 is a block diagram illustrating a configuration of the radiation therapy device controller according to the same embodiment.

In FIG. 2, reference numeral 1 indicates the radiation therapy device controller that controls the radiation therapy device 3, which irradiates a living body arranged between a ray source and a sensor array arranged in a position facing the ray source with radiation along an irradiation axis from the ray source to treat a diseased portion of the living body. Here, the ray source refers to a diagnostic X-ray source or a therapeutic radiation irradiation device. As shown in FIG. 2, the radiation therapy device controller 1 includes processing units of a CT image selection unit 102, a reconstructed image generation unit 103, a radiation projection image generation unit 104, a respiratory phase determination unit 105, a diseased portion tracking processing unit 106, a CT image updating unit 107, and a diseased portion position calculation unit 109, a control unit 101 that controls each processing unit, and a database 108 that stores information used for processing in each processing unit.

The CT image selection unit 102 is a processing unit that selects the CT image data from the CT image data group for each of a plurality of respiratory phases subjected to the updating process through the process of the CT image updating unit 107.

The reconstructed image generation unit 103 is a processing unit that generates, for a plurality of the rotation angles, the reconstructed image corresponding to the respiratory phase using the CT image data.

The radiation projection image generation unit 104 is a processing unit that generates a radiation projection image which shows the diseased portion when radiation is radiated from the ray source to the sensor array at a predetermined rotation angle.

The respiratory phase determination unit 105 is a processing unit that compares a reconstructed image for each of a plurality of respiratory phases with the generated radiation projection image and determines a respiratory phase indicated by the reconstructed image in which a difference between luminances of pixels constituting the images is small, to be a current respiratory phase of the living body.

The diseased portion tracking processing unit 106 is a processing unit that determines the position of the diseased portion calculated in advance in the CT image data in the CT image data group, of the respiratory phase determined based on the radiation projection image generated sequentially over time, to be a current position of the diseased portion.

The CT image updating unit 107 is a processing unit that performs the updating process using the initially set CT image data group for each respiratory phase generated in advance and recorded in the database 108 and creates a CT image data group (a reconstructed CT image data group) for each respiratory phase. The initially set CT image data group generated in advance and recorded in the database 108 may be a CT image data group generated by another device in advance or may be a CT image data group generated by the radiation therapy device controller 1 in advance.

The diseased portion position calculation unit 109 is a processing unit that calculates the position of the diseased portion in the CT image data updated by the CT image updating unit 107.

By including such a processing unit and database, the radiation therapy device controller 1 of the present embodiment performs control of accurately tracking the diseased portion moving in the living body on the radiation therapy device.

Figure 3:
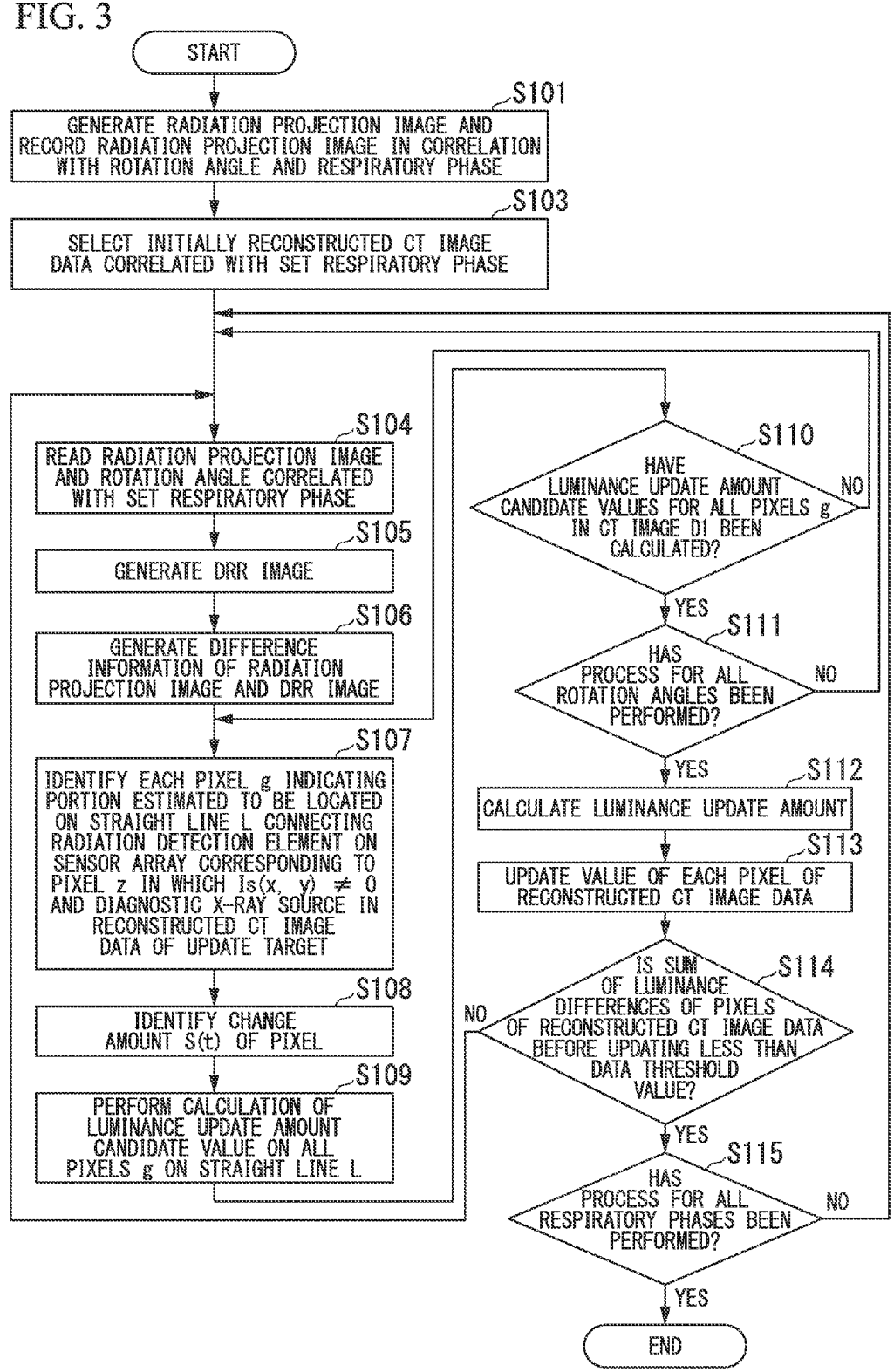
FIG. 3 is a diagram illustrating a process flow of the radiation therapy device controller.

Next, a process flow of the radiation therapy device controller 1 that controls the radiation therapy device 3 will be described step by step. FIG. 3 is a diagram illustrating a process flow of the radiation therapy device controller.

Hereinafter, the radiation projection image is assumed to be a radiation projection image generated by the radiation radiated toward the sensor array 32 by the diagnostic X-ray source 24. Further, the embodiment of the present invention similarly comes into effect even when another ray source and another sensor array that face each other are used.

Coordinates of the initially set CT image data and the reconstructed CT image data after the updating process is performed on the initially set CT image data are aligned based on a position of a spine or the like that rarely moves in a body motion prior to the present process flow.

First, the radiation therapy device controller 1 performs the process of updating the CT image data group recorded in the database 108 in advance. In the updating process, the CT image updating unit 107 instructs the radiation therapy device 3 to capture the radiation projection image including the diseased portion position.

Then, the diagnostic X-ray source 24 irradiates the living body with radiation, and the radiation therapy device controller 1 receives a signal detected by the sensor array 32 or data of the phase in a periodic motion of the infrared marker acquired by an infrared sensor, which is not shown. As described above, a period and phase of the periodic motion of the infrared marker correspond to a respiratory period and phase, and a CT image of each respiratory phase is created, as will be shown below, using the respiratory phase calculated based on the motion of the infrared marker.

Also, the CT image updating unit 107 generates a radiation projection image including the diseased portion position of the living body corresponding to a first rotation angle of rotation angles An (n=1 n). The CT image updating unit 107 records, in the database 108, the generated radiation projection image in correlation with the rotation angle and the information relating to the respiratory phase extracted from the data of the phase acquired by the infrared sensor when the radiation is radiated (step S101).

While the reconstructed CT image data is created in a plurality of respiratory phases by the CT image updating unit 107, a process in one respiratory phase (hereinafter referred to as a respiratory phase p1) will be hereinafter described.

Further, in the CT image updating unit 107, the CT image data is updated. CT image data set as an initial value is referred to as initially set CT image data. CT image data to be obtained by the updating process or CT image data in a process of calculating the CT image data to be obtained is referred to as reconstructed CT image data.

The CT image updating unit 107 reads the set respiratory phase p1 from a memory. Also, the CT image updating unit 107 selects CT image data $_sD1'$ recorded in correlation with a respiratory phase p1' closest to the set respiratory phase p1 from the initially set CT image data group recorded in the database 108, and uses the CT image data $_sD1'$ as initial reconstructed CT image data $_kD1$ (step S103). The CT image updating unit 107 then reads the radiation projection image and the rotation angle (rotation angle A1) recorded in correlation with the respiratory phase p1 among combination data of (the radiation projection image, the rotation angle, and the respiratory phase) recorded in the database 108 (step S104).

Figure 4:
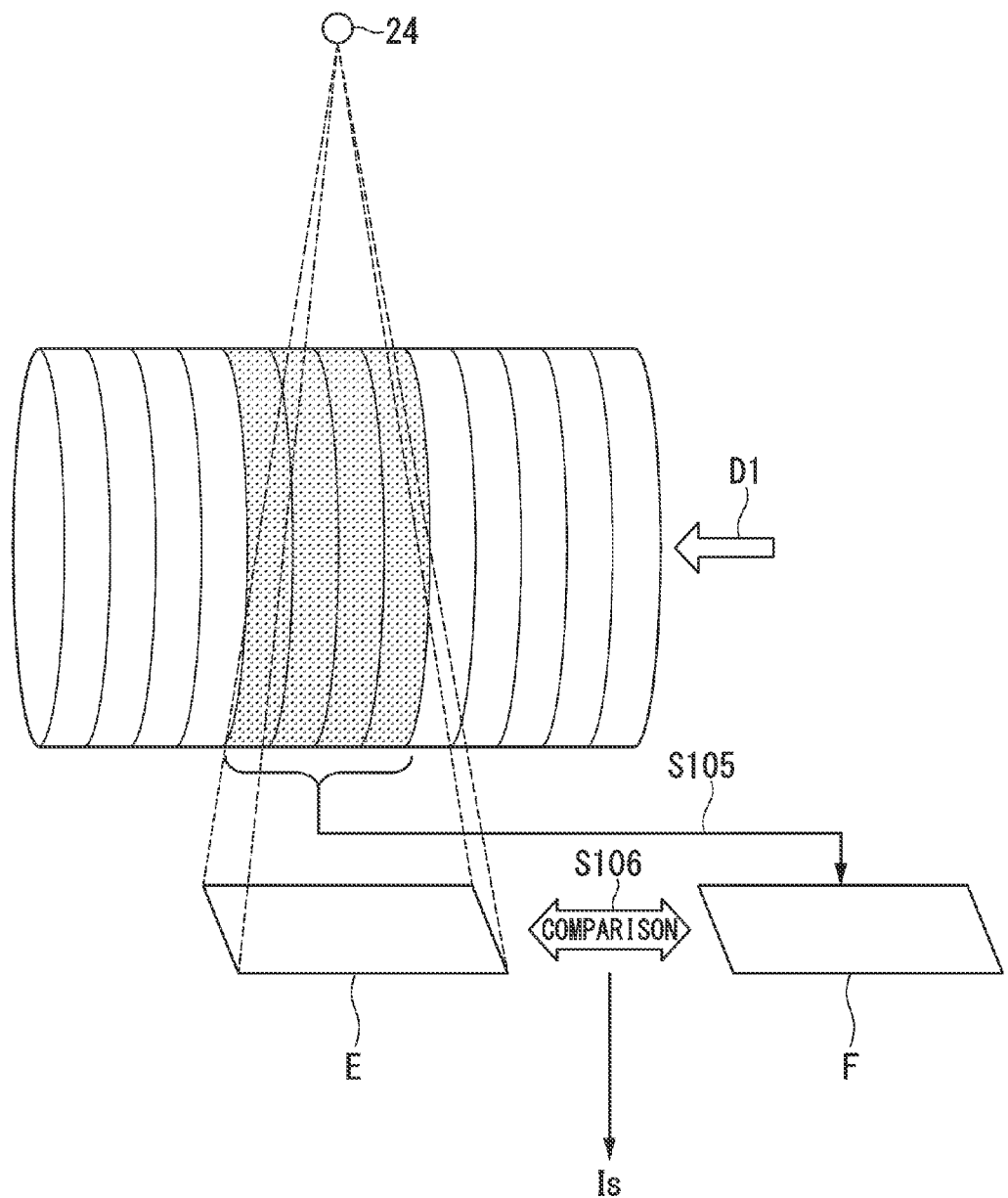
FIG. 4 is a diagram illustrating an overview of a difference information generation process.

FIG. 4 is a diagram illustrating an overview of a difference information generation process.

In FIG. 4, a radiation projection image E shows a radiation projection image corresponding to the rotation angle A1 identified by the CT image updating unit 107.

Hereinafter, the radiation projection image E is described as a radiation projection image (respiratory phase p1, rotation angle A1).

Next, the CT image updating unit 107 generates a reconstructed image using the selected reconstructed CT image data (step S105). In this case, the CT image updating unit 107 generates the reconstructed image when the radiation from the diagnostic X-ray source 24 is assumed to be projected when the rotation angle is A1.

A generation overview of the reconstructed image is shown in FIG. 4. The reconstructed image indicates, for example, a DRR (Digital Reconstructed Radiography) image. Hereinafter, the reconstructed image will be referred to as a DRR image F.

Further, the DRR image F generated in step S105 is described as a DRR image (respiratory phase p1, rotation angle A1). A method of generating the DRR image F is known technology. Also, when the DRR image (respiratory phase p1, rotation angle A1) is generated, the CT image updating unit 107 compares pixels of the radiation projection image (respiratory phase p1, rotation angle A1) with pixels of the generated DRR image (respiratory phase p1, rotation angle A1), and generates difference information indicating a luminance difference for the pixels (difference information in the case of the respiratory phase p1 and the rotation angle A1) (step S106).

More specifically, when a luminance value of the radiation projection image (respiratory phase p1, rotation angle A1) is Ik(x, y) and a luminance value of the DRR image is Id(x, y) (x and y indicate a position indicated by an x coordinate and a y coordinate from an origin of a pixel of each image), the difference information Is(x, y) can be represented by:

$$Is(x,y)=Id(x,y)-Ik(x,y).$$

That is, the difference information is information indicating a difference between the luminance values of pixels of the radiation projection image (respiratory phase p1, rotation angle A1) and the DRR image (respiratory phase p1, rotation angle A1). Here, if Is(x, y)≠0, it shows that there is a difference between information in a real living body from which the radiation projection image (respiratory phase p1, rotation angle A1) is generated and the reconstructed CT image data from which a DRR image (respiratory phase p1, rotation angle A1) is generated on the straight line L connecting the radiation detection element of the sensor array 32 corresponding to the pixel indicated by the coordinate (x, y) and the diagnostic X-ray source 24. Also, when the CT image updating unit 107 generates the difference information, the CT image updating unit 107 registers the difference information (respiratory phase p1, rotation angle A1) in the database 108.

When the difference information (respiratory phase p1, rotation angle A1) is generated, the CT image updating unit 107 reads the reconstructed CT image data $_k$D1 of an update target (which is used to create the DRR image among the CT images). Further, the CT image updating unit 107 reads the difference information (respiratory phase p1, rotation angle A1) and identifies a pixel z in which Is(x, y)≠0 in the difference information (respiratory phase p1, rotation angle A1). Next, the CT image updating unit 107 identifies each pixel g indicating a portion estimated to be located on a straight line L connecting the radiation detection element on the sensor array 32 corresponding to the pixel z and the diagnostic X-ray source 24 in the reconstructed CT image data $_k$D1 (step S107). Further, the CT image updating unit 107 reads the initially set CT image data $_s$D1' of the respiratory phase p1' (the respiratory phase closest to the respiratory phase p1 in the initially set CT image data group described above) from the database 108. The CT image updating unit 107 also reads initially set CT image data $_s$D2' that is at a closest phase p2' in a range of values smaller than the respiratory phase p1' indicated by the identified reconstructed CT image data D1 of an update target, from the database 108. Further, the CT image updating unit 107 reads initially set CT image data $_s$D3' that is at a closest phase p3' in a range of values greater than the respiratory phase p1' indicated by the CT image data D1 of the update target, from the database 108. As described above, the phases p2' and p3' are the closest phases in the range greater or smaller than the phase p1'. Therefore, $_s$D2', $_s$D1', and $_s$D3' of the CT image are initially set CT images corresponding to three successive respiratory phases in the initially set CT image data group.

Figure 5:
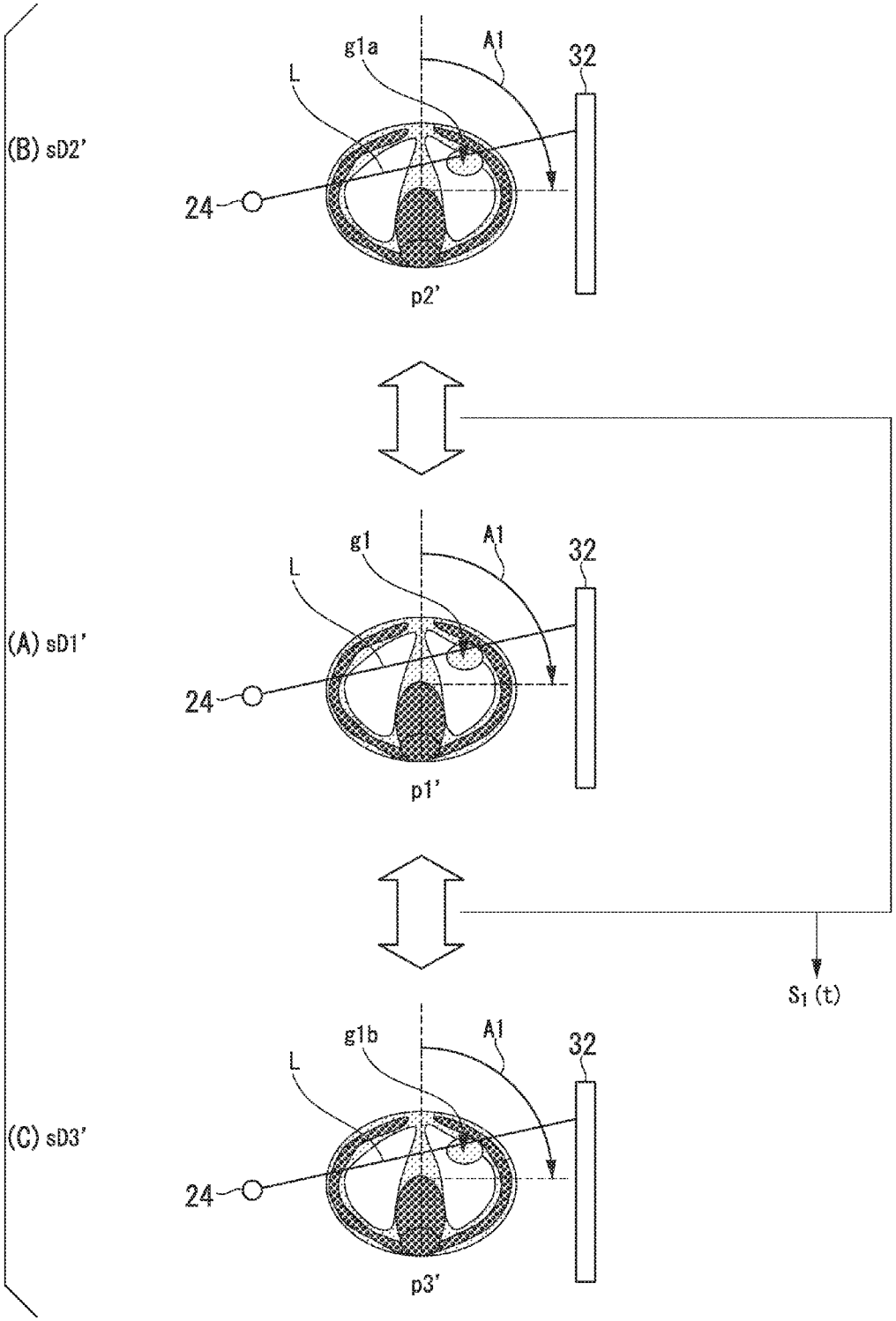
FIG. 5 is a diagram illustrating an overview of a process of calculating a change amount $S_1(t)$ of a pixel.

FIG. 5 is a diagram illustrating an overview of a process of calculating a change amount $S_1(t)$ of the pixel.

The CT image updating unit 107 calculates an absolute value d1 of a luminance difference between one pixel g1 among the pixels g of the identified initially set CT image data $_s$D1' (respiratory phase p1') and a pixel g1a corresponding to the pixel g1 in the initially set CT image data $_s$D2' (respiratory phase p2'), as shown in FIG. 5. Further, the CT image updating unit 107 calculates an absolute value d2 of a luminance difference between the one pixel g1 of the initially set CT image data $_s$D1' (respiratory phase p1') and a pixel g1b corresponding to the pixel g1 in the initially set CT image data $_s$D3' (respiratory phase p3'). Also, the CT image updating unit 107 identifies a greater value of the absolute value d1 and the absolute value d2 as the change amount $S_1(t)$ of the pixel g1 (step S108).

Here, a straight line L is L(t)=(Lx(t), Ly(t), Lz(t)), and t is defined as 0<t<1.

Further, the luminance value of the pixel g1 of the initially set CT image data D1' (respiratory phase p1') is D1'(Lx(t), Ly(t), Lz(t)).

Similarly, the luminance value of the pixel g1a of the initially set CT image data $_s$D2' (respiratory phase p2') is D2'(Lx(t), Ly(t), Lz(t)).

Similarly, the luminance value of the pixel g1b of the initially set CT image data $_s$D3" (respiratory phase p3') is D3'(Lx(t), Ly(t), Lz(t)).

Then, the change amount $S_1(t)$ can be represented by the following formula (1). Here, "max" is a function which takes a maximum value of an argument, and "abs" is a function which takes an absolute value of an argument. $S_1(t)$ represents a degree of easiness of change in luminance value of the pixel in the reconstructed CT image data. Here, a change amount of the luminance when the respiratory phase is changed is regarded as the degree of easiness of change in luminance.

[Formula 1]

$$S_1(t)=\max[\text{abs}\{D2'(Lx(t),Ly(t),Lz(t))-D1'(Lx(t),Ly(t),Lz(t))\},\text{abs}\{D3'(Lx(t),Ly(t),Lz(t))-D1'(Lx(t),Ly(t),Lz(t))\}] \quad (1)$$

This is a process of calculating a first change amount $S_1(t)$. Also, the CT image updating unit 107 performs the same calculation process in a plurality of pixels g identified as those indicating a portion estimated to be located on a straight line L connecting the radiation detection element on the sensor array 32 corresponding to the pixel z and the diagnostic X-ray source 24. Further, in order to improve resolution, it is desirable for this calculation process to be performed on all pixels. Hereinafter, the same calculation process is assumed to be performed in all the pixels.

In the above description, both the respiratory phase p2' and the respiratory phase p3' are used, but it is also possible to use only one of the respiratory phases.

Meanwhile, the CT image updating unit 107 may calculate a change amount S(t) by using a process of calculating a second change amount $S_2(t)$ or a process of calculating a third change amount $S_3(t)$, which will be described below, instead of the process of calculating a first change amount $S_1(t)$.

(Process of Calculating a Second Change Amount $S_2(t)$)

In the process of calculating a second change amount $S_2(t)$, the CT image updating unit 107 reads the difference information and identifies a pixel in which Is(x, y)≠0 in the difference information. Also, the CT image updating unit 107 identifies each pixel g1 corresponding to a portion estimated to be located on a straight line L connecting the radiation detection element on the sensor array 32 corresponding to the pixel and the diagnostic X-ray source 24, in the reconstructed CT image data $_k$D1 of an update target. The process up to this point is the same as the process of calculating a first change amount $S_1(t)$. Further, the CT image updating unit 107 reads initially set CT image data sD1' of the respiratory phase p1' from the database 108. Further, the CT image updating unit 107 reads a plurality of radiation projection images, including a radiation projection image generated at a rotation angle at which the respiratory phase differs from p1, from the database 108. Also, the CT image updating unit 107 generates CT image data D4 using the plurality of radiation projection images at the different rotation angles. The process of generating the CT image using the plurality of radiation projection images at the different rotation angles is a known technology.

Also, the CT image updating unit 107 identifies an absolute value of a luminance difference between a pixel g1 of the initially set CT image data sD1' (respiratory phase p1') read from the database 108 and a pixel g1c corresponding to the pixel g1 in the CT image D4 generated using the plurality of radiation projection images with the different rotation angles, as a change amount S(t) of the pixel g1. Also, if the luminance value of the pixel g1 of the initially set CT image data (respiratory phase p1') is D1'(Lx(t), Ly(t), Lz(t)) and the luminance value of the pixel g1c of the CT image D4 is D4(Lx(t), Ly(t), Lz(t)), the change amount $S_2(t)$ can be calculated by the following formula (2):

[Formula 2]

$$S_2(t)=\text{abs}\{D4(Lx(t),Ly(t),Lz(t))-D1'(Lx(t),Ly(t),Lz(t))\} \quad (2)$$

(Process of Calculating a Third Change Amount $S_3(t)$)

The process of calculating a first change amount $S_1(t)$ and the process of calculating a second change amount $S_2(t)$ are first performed in the process of calculating a third change amount $S_3(t)$. Also, using results of the process of calculating a first change amount $S_1(t)$ and the process of calculating a second change amount $S_2(t)$, the change amount $S_3(t)$ of the pixel g1 is calculated by a formula:

$$S_3(t)=\alpha S_1(t)+\beta S_2(t).$$

α and β are coefficients. For example, calculation in which α=0.5 and β=0.5 is performed.

Figure 6:
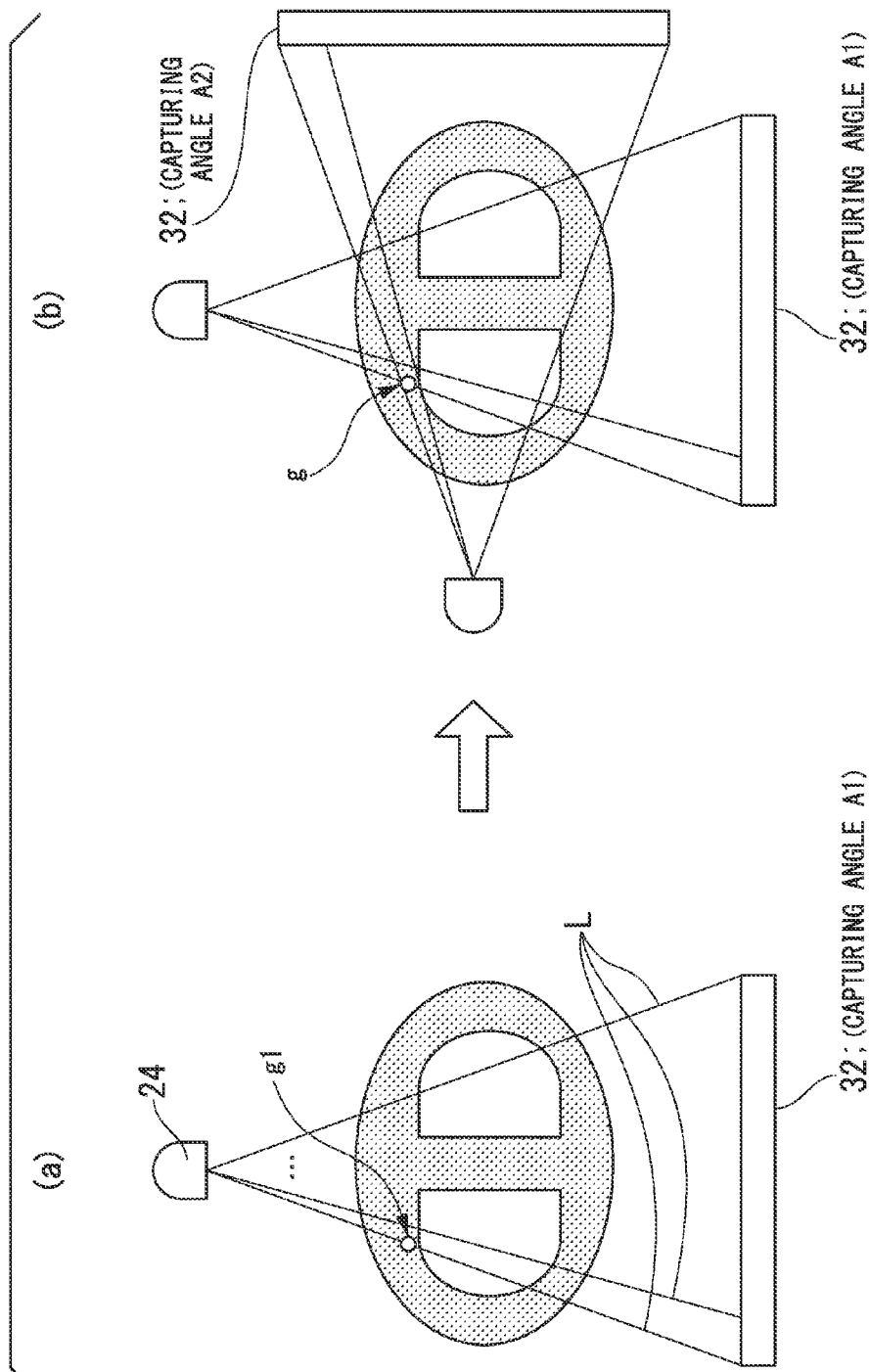
FIG. 6 is a diagram illustrating an overview of a process of calculating a luminance update amount.

FIG. 6 is a diagram illustrating an overview of a process of calculating a luminance update amount.

As shown in FIG. 6(a), if the process of calculating any one of the first to third change amounts S(t) is finished, the CT image updating unit 107 calculates a sum (ΣS(t)) of change amounts S(t) calculated for all the pixels g. Further, the CT image updating unit 107 calculates a ratio (S(t)÷ΣS(t)) of the change amount S(t) calculated for one pixel g1 corresponding to a certain portion on the straight line L to the sum of change amounts S(t). Also, the CT image updating unit 107 multiplies the ratio of S(t) by the luminance difference Is indicated by the difference information calculated for the pixel z. In this way, the CT image updating unit 107 calculates a luminance update amount candidate value that is a value obtained by distributing information of a difference represented by the luminance difference calculated for the pixel z to one pixel g1 corresponding to a portion estimated to be on the straight line L of the CT image data D1. This luminance update amount candidate value is R(x, y, z). This process is performed on all the pixels g on the straight line L (step S109).

If the processing of the luminance update amount candidate value is finished, the CT image updating unit 107 determines whether the luminance update amount candidate value has been calculated for all radiation detection elements (pixels) on the sensor array 32 (step S110), and repeats the process of steps S107 to S109 described above if the luminance update amount candidate value has not been calculated.

If the answer is "yes" in step S110, the CT image updating unit 107 determines whether the process has been performed on all rotation angles recorded in the database 108 in correlation with the respiratory phase p1 that is a target (step S111). If the process has not been performed on all the rotation angles recorded in the database 108 in correlation with the respiratory phase p1 that is a target, the CT image updating unit 107 changes the rotation angle A1, sets a next rotation angle A2, instructs to start the process of steps S103 to S110 described above using the radiation projection image of the rotation angle A2, and repeats the process up to the rotation angle An. Through the above process, a plurality of difference information of the respiratory phase p1 and the rotation angles A1 to An, and the luminance update amount candidate value R(x, y, z) of the pixel in the reconstructed CT image data $_k$D1 of each combination of the respiratory phase p1 and the rotation angles A1 to An are recorded in the database 108.

Next, the CT image updating unit 107 calculates the luminance update amount of each pixel whose luminance update amount candidate value has been calculated, in the reconstructed CT image data $_k$D1, using the luminance update amount candidate value for each pixel in the reconstructed CT image data $_k$D1 calculated for each of the rotation angles A1 to An for the respiratory phase p1 (step S112).

More specifically, as shown in FIG. 6(b), the CT image updating unit 107 calculates an average of the luminance update amount candidate value R(x, y, z) calculated for each of the rotation angles A1 to An for a pixel in the reconstructed CT image data $_k$D1 of the respiratory phase p1, as the luminance update amount.

Alternatively, if the radiation projection image generated in step S101 for each repeated process at the rotation angles A1 to An based on the determination of step S111 is generated at a timing of a different respiratory phase, the CT image updating unit 107 may calculate the luminance update amount by performing weighting in such a manner that a weight of the luminance update amount candidate value R(x, y, z) when the process of steps S102 to S109 is performed using the radiation projection image generated at a timing of the respiratory phase closest to the respiratory phase indicated by the reconstructed CT image data $_k$D1 is greatest. For example, if the respiratory phase indicated by the reconstructed CT image data $_k$D1 is p and the luminance update amount candidate value calculated using the radiation projection image in which the rotation angle is Ai and the respiratory phase is pi is Ri, the luminance update amount D of the pixel g(x, y, z) whose luminance update amount candidate value in the reconstructed CT image data $_k$D1 has been calculated is calculated by:

[Formula 3]

$$D(x,y,z)=\Sigma\{(\omega i \cdot Ri)\div\Omega\} \quad (3)$$

Here, Ω in Formula (3) shows $\Omega = \Sigma \omega i$. For example, ωi is

[Formula 4]

$$\omega i = 1 \div (abs(p - pi) + 1) \quad (4)$$

The CT image updating unit 107 adds the luminance update amount D calculated for each pixel whose luminance update amount candidate value in the reconstructed CT image data $_kD1$ has been calculated to a value of the corresponding pixel in the reconstructed CT image data $_kD1$ of the respiratory phase p1 that is a target to update the value of each pixel of the reconstructed CT image data $_kD1$ and update the reconstructed CT image data into the reconstructed CT image data $_{k+1}D1$ (step S113). Next, the CT image updating unit 107 compares the reconstructed CT image data $_{k+1}D1$ after the updating process with the reconstructed CT image data $_kD1$ before the updating process. In this comparison process, a luminance difference between a certain pixel of the reconstructed CT image data $_{k+1}D1$ after the updating process and the pixel of the reconstructed CT image data $_kD1$ before the updating corresponding to the certain pixel is calculated for all corresponding pixels, and it is determined whether a sum thereof is less than a threshold value (step S114). Also, if the sum is less than the threshold value, the CT image updating unit 107 determines that the process is finished using the reconstructed CT image data D1 after the updating process. If the sum is greater than or equal to the threshold, the CT image updating unit 107 repeats the process from step S104 ($_k$ of $_{k+1}D1$ is updated into $_{k+1}D1$). In the repeated process, the reconstructed CT image data ($_{k+1}D1$) after the updating process is used.

Further, if the sum is less than the threshold in step S114, it is determined whether the process of steps S102 to S114 has been performed on all respiratory phases pm (m=1 m) that are reconstructed CT image data creation targets (step S115). If the process has not been performed, the process of steps S101 to S114 is performed on other respiratory phases. Accordingly, the process of updating the reconstructed CT image data for all the respiratory phases pm that are reconstructed CT image data creation targets is finished.

Here, according to the process of updating the CT image described above, the process of updating the data is performed using the CT image data group (initially set CT image data group) created in advance and recorded in the database 108. Accordingly, it is possible to obtain a high-quality CT image in a short time by performing only the above-described updating process using the newly generated radiation projection image. Also, it is possible to irradiate a diseased portion position with the radiation with high accuracy by performing the process of tracking the diseased portion using the high-quality CT image.

Further, according to the process described above, since the luminance update amount only for each pixel whose luminance update amount candidate value has been calculated is calculated and the process of updating the CT image is performed using the luminance update amount, it is not necessary to perform the updating process on the pixel whose luminance update amount candidate value has not been calculated. Accordingly, it is possible to shorten a time to complete the updating process by pixels on which the updating process is not performed.

Figure 7:
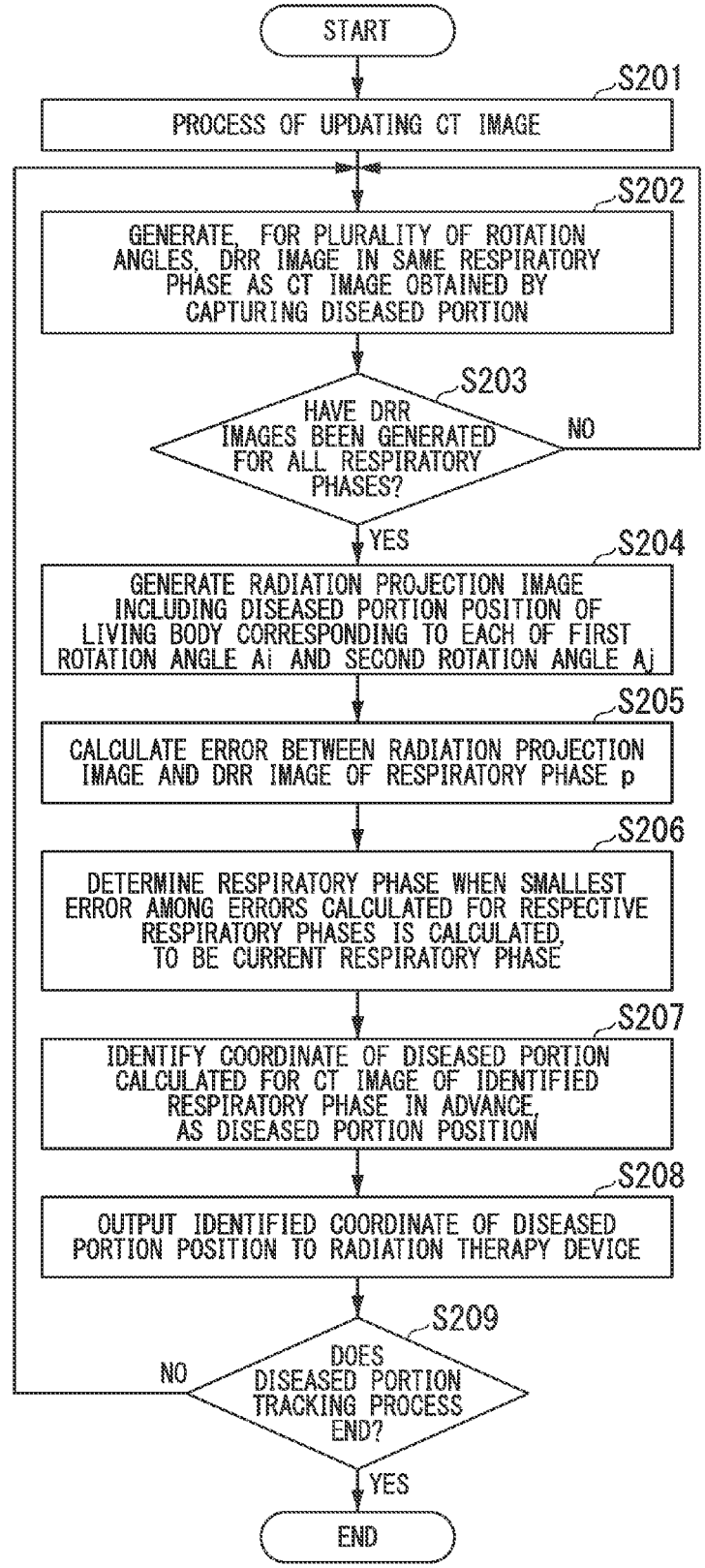
FIG. 7 is a diagram illustrating a process flow in a diseased portion tracking process.

FIG. 7 is a diagram illustrating a process flow in a diseased portion tracking process.

FIG. 8 is a diagram illustrating an overview of a diseased portion tracking process.

When the process of updating the CT image data group is finished (step S201), a user identifies a range of the diseased portion in the CT image subjected to the updating process for any respiratory phase or all respiratory phases. Information of the range of the diseased portion in the CT image is registered in correlation with identification information of the CT image in the database 108. Also, the user inputs completion of identifying of the diseased portion position to the radiation therapy device controller 1. Further, when the information of the range of the diseased portion only in the CT image subjected to the updating process for any respiratory phase has been identified by the user, the diseased portion position calculation unit 109 detecting the input of the completion of specifying of the diseased portion position identifies the range of the diseased portion in the CT images of the other respiratory phases in which the range of the diseased portion has not been identified. Also, the coordinates of the center of the range of the diseased portion in the CT image in which the range of the diseased portion has been identified is registered in the database 108 in correlation with the identification information of the CT image. In the process of identifying the diseased portion in the respiratory phase in which the range of the diseased portion has not been identified by the user, the diseased portion position calculation unit 109 reads pixel data of the diseased portion range selected by the user from the CT image and searches for a range similar to the pixel data in a CT image of the other phase to identify the range of the diseased portion in the CT image of the respiratory phase that is a target. Also, the diseased portion position calculation unit 109 calculates, as the diseased portion position, a central coordinate C of the range of the diseased portion in the identified CT image. If a luminance value of a coordinate of the diseased portion range T selected by the user is C(x, y, z) (where (x, y, z)∈T) and a luminance value of a pixel in a range corresponding to the diseased portion range in the CT image of the other phase is c'(x, y, z),

[Formula 5]

$$\sum_{(x,y,z) \in T} (c'(x + p, y + q, z + r) - c(x, y, z))^2 \quad (5)$$

a coordinate (p, q, r) corresponding to the central coordinate C at which this formula is minimized is obtained, the coordinate (p, q, r) is used as an amount of a movement from the diseased portion range T selected by the user, and the center coordinate of the range corresponding to the diseased portion range of the CT image of the other phase is calculated as the diseased portion position.

Next, the CT image selection unit 102 selects, for each of a plurality of respiratory phases, a CT image from the CT image data group after the updating process. Also, the reconstructed image generation unit 103 generates, for a plurality of rotation angles, a DRR image in the same respiratory phase as the selected CT image using the plurality of CT images that are update targets (step S202). Further, based on the selected CT images of all respiratory phases, the reconstructed image generation unit 103 similarly reads the CT image of the update target and generates, for each of the plurality of rotation angles, the DRR image of each respiratory phase (see FIG. 8(a)). The DRR image is recorded in the database 108 by the reconstructed image generation unit 103. Also, each time the reconstructed image generation unit 103 generates the DRR image and records the DRR image in the database 108, the reconstructed image generation unit 103 determines whether the DRR images for all the respiratory phases that are targets have been generated for each rotation angle (step S203) and proceeds to the next step if the DRR images have been generated.

The radiation therapy device controller 1 performs the process of tracking the diseased portion using the DRR image corresponding to the respiratory phase of each of the plurality of rotation angles generated using the CT image data group after the updating process described above. Also, the control device 1 for a radiation therapy device controls the radiation therapy device 3 to perform radiation irradiation on the tracked diseased portion.

In the process of tracking the diseased portion, the radiation projection image generation unit 104 starts generation of the radiation projection image of the living body secured in a position on the treatment table 41 of the radiation therapy device 3 in the same manner in which the CT image data group has been generated. Then, the radiation projection image generation unit 104 instructs the radiation therapy device 3 to capture the radiation projection image of a plurality of predetermined rotation angles including the diseased portion position. For example, the plurality of predetermined rotation angles is assumed to be a first rotation angle Ai and a second rotation angle Aj. Here, the first rotation angle Ai and the second rotation angle Aj are assumed to be values matching the rotation angles indicated by any one of the DRR images generated in step S202.

Next, the radiation therapy device 3 irradiates the living body with radiation in the first rotation angle Ai and the second rotation angle Aj. Further, the radiation therapy device controller 1 receives a signal detected by the sensor array 32 based on the irradiation of the radiation. Also, the radiation projection image generation unit 104 generates the radiation projection image including the diseased portion position of the living body corresponding to each of the first rotation angle Ai and the second rotation angle Aj of the traveling gantry 14 (step S204) and records the radiation projection image in the database 108 (see FIG. 8(b)). Further, until radiation therapy is finished, the radiation therapy device controller 1 instructs, every predetermined time interval, the radiation therapy device 3 to capture the radiation projection image, and repeats a radiation projection image generation process every predetermined time interval based on information received from the radiation therapy device 3. The radiation projection image is recorded in the database 108 by the radiation projection image generation unit 104.

If the generation of the radiation projection image including the diseased portion position of the living body corresponding to each of the first rotation angle Ai and the second rotation angle Aj is completed, the respiratory phase determination unit 105 determines the current respiratory phase of the living body using the generated radiation projection image, and the DRR image corresponding to the respiratory phase of each rotation angle generated in advance. Specifically, first, the respiratory phase determination unit 105 reads the radiation projection image of the first rotation angle Ai, and the plurality of DRR images of different respiratory phases generated as images of the rotation angle Ai from the database 108. Further, the respiratory phase determination unit 105 reads the radiation projection image of the second rotation angle Aj, and the plurality of DRR images of different respiratory phases generated as images of the rotation angle Aj from the database 108. Also, the respiratory phase determination unit 105 compares the radiation projection image of the first rotation angle Ai with the DRR image of the respiratory phase p in the first rotation angle Ai. Further, the respiratory phase determination unit 105 compares the radiation projection image of the second rotation angle Aj with the DRR image of the respiratory phase p in the second rotation angle Aj (see FIGS. 8(b) and (c)). Also, the respiratory phase determination unit 105 calculates an error between the radiation projection image and the DRR image of the respiratory phase p through the comparison process (step. S205).

Here, the radiation projection image of the first rotation angle Ai is Ik(x, y) and the DRR image of the respiratory phase p among the DRR images of the rotation angle Ai is Id(x, y, p). Further, the radiation projection image of the second rotation angle Aj is I'k(x', y') and the DRR image of the respiratory phase p among the DRR images of the rotation angle Aj is I'd(x', y', p). Also, the respiratory phase determination unit 105 calculates the error between the radiation projection image and the DRR image of the respiratory phase p using the following formula (6).

[Formula 6]

$$\sum_{X,Y \in \text{ entire image range}} \left\{ \begin{array}{l} (Ik(X, Y) - Id(X, Y, p))^2 + \\ (I'k(X', Y') - I'd(X', Y', p))^2 \end{array} \right\} \quad (6)$$

Further, the respiratory phase determination unit 105 calculates an error between the radiation projection image and the DRR image of the respiratory phase p for a plurality of respiratory phases p (p=1 ... pm) using Formula (6). Also, the respiratory phase determination unit 105 determines that the respiratory phase when the smallest error among the errors calculated for the respective respiratory phases is calculated is a current respiratory phase (step S206).

Formula (6) is used to calculate, for all pixels in the image, luminance differences of the pixels of the entire images of the radiation projection image and the DRR image and calculate the error between the radiation projection image and the DRR image of the respiratory phase p using a sum of the calculated luminance differences of the respective pixels. However, the respiratory phase determination unit 105 may calculate the error between the radiation projection image and the DRR image of the respiratory phase p using the sum only in a pixel range in which the luminance difference is great. For example, the DRR images of a plurality of respiratory phases p (p=1 ... pm) indicating the rotation angle Ai are compared, and a pixel in which a difference between a maximum luminance and a minimum luminance for the pixels in the same position is greater than or equal to a threshold C is identified as a pixel range candidate in which the luminance difference is great. Also, for example, if a range formed by the unity of the pixels identified as the pixel range candidate is greater than or equal to a predetermined area, the respiratory phase determination unit 105 determines that the pixel range candidate is included in the pixel range S in which the luminance difference is great. Further, similarly, the DRR images of a plurality of respiratory phases p (p=1 ... pm) indicating the rotation angle Aj are compared, and a: pixel range S' in which the luminance difference of the respective DRR images in the rotation angle Aj is great is determined. Also, the error between the radiation projection image and the DRR image of the respiratory phase p is calculated using Formula (7).

[Formula 7]

$$\sum_{X,Y \in S} \{(Ik(X, Y) - Id(X, Y, p))^2\} + \sum_{X',Y' \in S'} \{(I'k(X', Y') - I'd(X', Y', p))^2\} \quad (7)$$

Thus, it is possible to identify the respiratory phase of the living body when the radiation projection image is generated.

Further, the diseased portion tracking processing unit 106 reads the coordinate of the diseased portion calculated for the CT image of the identified respiratory phase in advance from the database 108, and identifies the coordinate as the diseased portion position (step S207). Further, the diseased portion tracking processing unit 106 outputs the identified coordinate of the diseased portion position to the radiation therapy device 3 (step S208). Accordingly, the radiation therapy device 3 performs such a control that the radiation hits a space coordinate corresponding to the coordinate of the diseased portion position, and radiates the radiation. Also, it is determined whether the diseased portion tracking process is finished or not (step S209), and if the diseased portion tracking process is finished (Yes), the process is repeated from step S202.

The embodiments of the present invention have been described above. According to the process described above, since the current respiratory phase is sequentially identified using the radiation projection image generated sequentially at the time of treatment and the DRR image, and the diseased portion position identified in advance for the CT image corresponding to the identified respiratory phase is identified as a current diseased portion position, it is possible to improve the accuracy of tracking the diseased portion moving in the living body.

In the above embodiment, the radiation projection image has been shown by the example in which the radiation projection image is created based on the ray source and the sensor array included in the radiation therapy device. However, the radiation projection image may be created, for example, by a diagnostic device (a CT or an MRI) included separately from the radiation therapy device.

Further, the radiation therapy device controller or the radiation therapy device described above includes a computer system therein. Also, the process of each processing described above is stored in a computer-readable recording medium in the form of a program. As this program is read and executed by the computer, the processing is performed. Here, the computer-readable recording medium refers to a magnetic disk, a magneto-optical disc, a CD-ROM, a DVD-ROM, a semiconductor memory, or the like. Further, this computer program may be distributed to a computer through a communication line, and the computer receiving this distribution may execute the program.

Further, the above program may be a program for realizing some of the above-described functions.

Further, the program may be a program that can realize the above-described functions in combination with a program already recorded in the computer system, i.e., may be a so-called differential file (differential program).

INDUSTRIAL APPLICABILITY

Since it is possible to create a CT image immediately before treatment based on the CT image in which the diseased portion position has been identified in advance, it is possible to easily identify the diseased portion position immediately before treatment and to achieve improvement of accuracy of tracking a diseased portion moving in the living body.

DESCRIPTION OF REFERENCE NUMERALS

1 . . . radiation therapy device controller
3 . . . radiation therapy device
101 . . . control unit
102 . . . CT image selection unit
103 . . . reconstructed image generation unit
104 . . . radiation projection image generation unit
105 . . . respiratory phase determination unit
106 . . . diseased portion tracking processing unit
107 . . . CT image updating unit
108 . . . database
109 . . . diseased portion position calculation unit

The invention claimed is:

1. A processing method for a radiation therapy device controller for controlling a radiation therapy device that irradiates a living body arranged between a ray source and a sensor array with radiation from the ray source to treat a diseased portion of the living body, the processing method comprising:

selecting, for each of a plurality of body motion phases of the living body, computed tomography image data from a computed tomography image data group generated for each of the plurality of body motion phases of the living body;

generating, for each rotation angle of the ray source and the sensor array, a reconstructed image corresponding to the body motion phase using the selected computed tomography image data;

generating a radiation projection image which shows the diseased portion when the radiation is radiated from the ray source to the sensor array if the rotation angle is a predetermined rotation angle;

comparing the reconstructed image of each of the plurality of body motion phases with the the generated radiation projection image, and determining the body motion phase indicated by a reconstructed image in which a difference between luminances of pixels constituting the images is small, to be a current body motion phase of the living body; and identifying a position of the diseased portion calculated for the CT image data in the CT image data group of the current body motion phase of the living body in advance, and determining the identified position to be a current position of the diseased portion.

2. A non-transitory computer-readable storage medium storing a program for causing a computer of a radiation therapy device controller for controlling a radiation therapy device that irradiates a living body arranged between a ray source and a sensor array with radiation from the ray source to treat a diseased portion of the living body, to function as:

a computed tomography image selection device that selects, for each of a plurality of body motion phases of the living body, computed tomography image data from a computed tomography image data group generated for each of the plurality of body motion phases of the living body;

a reconstructed image generation device that generates, for each rotation angles of the ray source and the sensor array, a reconstructed image corresponding to the body motion phase using the selected computed tomography image data;

a radiation projection image generation device that generates a radiation projection image which shows the diseased portion when the radiation is radiated from the ray source to the sensor array if the rotation angle is a predetermined rotation angle;

a body motion phase determination device that compares the reconstructed image of each of the plurality of body motion phases with the generated radiation projection image, and determines the body motion phase indicated by a reconstructed image in which a difference between luminances of pixels constituting the images is small, to be a current body motion phase of the living body; and a diseased portion tracking processing device that identifies a position of the diseased portion calculated for the computed tomography image data in the computed tomography image data group of the current body motion phase of the living body in advance, and determines the identified position to be a current position of the diseased portion.

* * * * *